United States Patent [19]

Antonucci

[11] Patent Number: 4,616,073

[45] Date of Patent: Oct. 7, 1986

[54] HYDROPHOBIC DENTAL COMPOSITES BASED ON A POLYFLUORINATED DENTAL RESIN

[75] Inventor: Joseph M. Antonucci, Kensington, Md.

[73] Assignee: The United States of America as represented by the Department of Health and Human Services, Washington, D.C.

[21] Appl. No.: 639,673

[22] Filed: Aug. 9, 1984

[51] Int. Cl.$^4$ ..................... A61C 13/08; C08F 214/18
[52] U.S. Cl. ................................. 526/246; 433/212.1; 526/245
[58] Field of Search ................. 526/245, 246

[56] References Cited

U.S. PATENT DOCUMENTS

| | | | |
|---|---|---|---|
| 2,464,120 | 3/1949 | Dickey et al. | 526/245 |
| 2,642,416 | 6/1953 | Ahlbrecht et al. | 260/83.5 |
| 3,055,932 | 9/1962 | Verbanic et al. | 526/245 |
| 3,062,765 | 11/1962 | Sherman et al. | 260/29.6 |
| 3,540,126 | 11/1970 | Chang et al. | 260/85.5 |
| 3,637,614 | 1/1972 | Greenwood | 260/80.72 |
| 3,639,361 | 2/1972 | Robertson et al. | 526/245 |
| 3,698,856 | 10/1972 | Pittman et al. | 260/2.5 |
| 3,808,179 | 4/1974 | Gaylord | 260/86.1 |
| 3,926,906 | 12/1975 | Lee, II et al. | 260/86.1 |
| 3,950,315 | 4/1976 | Cleaver | 260/42.53 |
| 3,991,008 | 11/1976 | Temin et al. | 260/42.15 |
| 3,997,504 | 12/1976 | Plymale | 526/245 |
| 4,043,965 | 8/1977 | Dickson | 260/29.6 |
| 4,067,853 | 1/1978 | Schmitt et al. | 260/47 |
| 4,097,994 | 7/1978 | Reaville et al. | 260/47 |
| 4,127,711 | 11/1978 | Lore et al. | 260/86.1 |
| 4,130,706 | 12/1978 | Plambeck, Jr. | 526/245 |
| 4,292,029 | 9/1981 | Craig et al. | 526/245 |
| 4,379,695 | 4/1983 | Orlowski et al. | 433/228 |
| 4,388,448 | 6/1983 | Melby | 433/217 |

*Primary Examiner*—Harry Wong, Jr.
*Attorney, Agent, or Firm*—Browdy and Neimark

[57] ABSTRACT

Dental resin systems prepared from polyfunctional or monofunctional highly-fluorinated methacrylate prepolymers are described. Preferred systems comprise (a) a major amount of a polyfluorinated aligomeric polyfunctional methacrylate such as (PFMA), preferably in combination with a diluent monomer such as 1,10-decamethylene dimethacrylate (DMDMA), methyl methacrylate (MMA), neopentyl dimethacrylate (NPDMA), 1,6-hexamethylene dimethacrylate (HMDMA), etc., or mixtures thereof; and (b) a minor amount of a polyfluorinated monofunctional methacrylate (PFMMA), such as 1,1-dihydropentadecafluorooctyl methacrylate (PDFOMA) as a minor or secondary diluent monomer in a non-hydroxylated bis-GMA resin system. The products are generally useful as hydrophobic dental materials, esepcially as composited (with fillers), sealants and cements.

5 Claims, No Drawings

HYDROPHOBIC DENTAL COMPOSITES BASED ON A POLYFLUORINATED DENTAL RESIN

FIELD OF THE INVENTION

The present invention concerns the field of dentistry, and especially relates to improved dental restorations.

BACKGROUND OF THE INVENTION

Composite restorative materials are finding ever-increasing use in dentistry. Although current composites are designed primarily for use as restorations for anterior and other non-load-bearing regions of tooth structure, these materials (perhaps prematurely) are being applied to the posterior acclusal region as well. As anterior restorative materials, many of the current composites have performed reasonably well, although clinical and other studies have shown that these esthetic filling materials have several significant shortcomings; namely, color instability, lack of stain resistance, marginal leakage and chemical erosion which contributes to anatomic loss.

The susceptibility of the organic matrix to chemical disintegration is a likely critical factor contributing to the wear of dental composites both in stress-bearing and stress-free applications. The complex interaction of composite restorations with the many chemical substances (e.g. $H_2O$, $O_2$, food-related chemicals, etc.) found in the oral environment, can by diffusion-controlled processes initially lead to plasticization, and ultimately to chemical degradation of the polymer matrix. Since they exists in a predominantly aqueous environment, the transport of other chemical substances into the polymer phase is likely to be water-assisted.

The solubility parameter of the dental resin system employed for restorative materials, its water-related properties (e.g., water sorption), and its degree of polymerization and crosslinking, are important factors governing the extent of chemical softening and disintegration that will occur in dental composites. The relatively hydrophilic matrices of conventional bis-GMA (2,2,-bis[4'(3"-methacroyl-2"-hydroxypropoxy)phenyl]propane) or urethane methacrylate copolymer systems have solubility parameters similar to certain chemical substances (e.g. food derived chemicals) found in the oral cavity. Composites based on these resin systems, therefore, will display an affinity not only for water but also for many of the chemical moieties generated intraorally. The complex sorption/desorption processes that occur in these composites may induce not only stresses but also degenerative chemical reactions that accelerate the failure of these restorative materials.

U.S. Pat. No. 4,292,029 to Craig et al employs a large amount of fluorinated alkyl methacrylate (1,1,5-trihydrooctafluoropentyl methacrylate, OFPMA) in conjunction with an analog of bis-GMA in an attempt to overcome the drawbacks of the conventional bis-GMA resin system. The hydrophobic composite represents a significant advance in designing an esthetic restorative material with enhanced resistance to the assaults of the oral environment. The dental resin system suffers however from several serious deficiencies, namely (a) loss of OFPMA on mixing because of its relatively high vapor pressure and its greater potential for irritation than a bulky fluorinated monomer of low vapor pressure; (b) undesirably greater opacity than desirable because of the relatively low refractive index of OFPMA and (c) low strength.

The relatively low crosslinked density of the OFPMA polymeric matrix results in composites of relatively low strength which fail to meet the minimum requirement for diametral tensile strength (34 MPA) established by the American Dental Association. In addition, such composite materials exhibit a relatively high contraction on polymerization. Craig mentions but does not give actual examples of composites derived from fluorinated bis-GMA analogs or other fluorinated dimethacrylates (e.g. tetrafluoroethylene glycol dimethacrylate); the existence of the latter is doubtful. Also, the use of fluorinated silane agents is mentioned, but again, no examples of how they are used are given. The fluorinated silane agents (e.g. hydrooctafluorobutyltrichlorosilane) cited are actually not coupling agents and their sole or improper use leads to extremely weak composites. Only the dual silanization procedure disclosed below leads to strong composites having excellent compatibility of the resin and filler components.

SUMMARY OF THE INVENTION

Accordingly, the invention relates to improved hydrophobic dental resin systems, especially such systems containing a high concentration of fluorinated monomers. More generally, it is an object of the invention to overcome deficiencies in the prior art, such as indicated above; and to provide for improved dental materials and their use.

Composites based on such dental resin systems have polymeric matrices that are highly immune to chemical softening and chemical degradation. The composites are not readily wet by water or saliva; exhibit extremely low water sorption and marginal leakage; and are also relatively oleophobic, which further enhances their resistance to surface staining; and have lesser opacity because of higher refraction index (compared to OFPMA). Further, and importantly, the composites demonstrate low polymerization shrinkage, which tends to generate stress points at composite-cavity wall interfaces.

In particular, the invention relates to the use of bulky, highly fluorinated methacrylate monomers in preparing dental resin systems having reduced water sorption and polymeric shrinkage characteristics but at least adequate strength. The use of 1,1 dihydropentadecafluorooctyl methacrylate (PDFOMA), a bulky highly fluorinated monomethacrylate (PFMMA), with PFMA, a bulky highly fluorinated multifunctional methacrylate according to formula II below and known as PFMA:

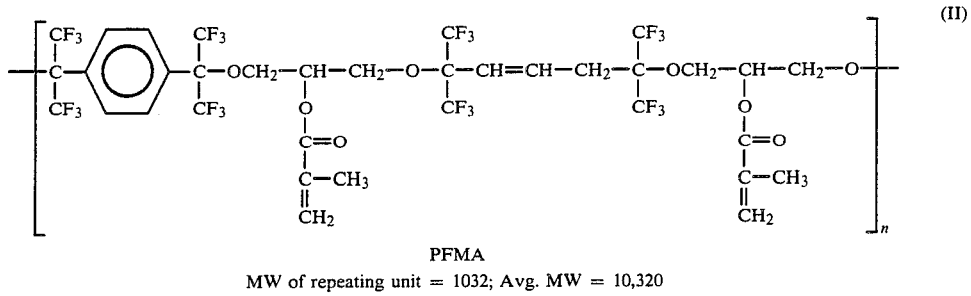

PFMA
MW of repeating unit = 1032; Avg. MW = 10,320
Average Percent F = 44.2, is uniquely different from the prior art dental resins.

The PFMA prepolymers employed herein are highly fluorinated, multiacrylated monomers which comprise fluorinated analogs of the widely used bis-GMA or of similar difunctional or multifunctional, non-fluorinated prepolymer monomers (e.g. urethane derivatives of bis-GMA derived from bis-GMA and diisocyanates such as 1,6-hexamethylene diisocyanate). Both types of multifunctional monomers yield polymeric matrices that are highly cross-linked. However, the present fluorinated, crosslinking or thermosetting monomers, in addition impart a low surface energy character to the matrices similar to that of fluorocarbon polymers such as poly(tetrafluoroethylene). Such low surface energy polymeric matrices are highly resistant to the absorption of aqueous fluids (i.e. they are hydrophobic) and to staining by food derived products (e.g. they tend to be oleophobic).

The crosslinking nature of these highly fluorinated resins is important because it reduces the solubility of the resin components and leads to composite and sealant materials of enhanced strength, excellent dimensional stability, excellent chemical resistance, and extremely low permeability to fluid penetration. These features are especially critical if dental composite and sealant materials are to have a long service life in the oral environment. By contrast, currently used resin-based dental materials have a relatively high permeability to oral fluids which leads to chemical softening or plasticization and ultimately to degradation of the composite or sealant.

PFMA is preferably a prepolymer product. The prepolymer product is both highly fluorinated and multifunctional, and possesses an extremely high molecular weight, but yet has a relatively modest viscosity for its great bulk. This oligomeric or prepolymer compound is compatible with a wide range of both hydrocarbon and fluorocarbon diluent monomers, and thus, it is possible to vary the content of covalently bound fluorine in the dental resin over a wide range. Because of its bulky nature and the minimal amounts of diluent monomer needed to obtain dental resins of workable viscosities, PFMA based resins yield dental composite and sealant materials having very low shrinkage on polymerization. This latter property is of importance because of this very modest polymerization contraction leads to composites and sealants with less residual stresses and, also, improves margin adaptability of the material to the cavity walls, thereby reducing the potential for microleakage and the formation of secondary caries.

The systems comprising PFMMA employed herein are single-phase resin systems based on non-hydroxylated derivatives of bis-GMA and including a minor portion of fluorinated monofunctional alkyl methacrylate, especially PDFOMA, as diluent. These systems exhibit characteristics comparable to the systems comprising PFMA described supra. Both systems are useful in a variety of dental applications including composites, cements, and sealants. The refractive indices of dental resins based on PFMA and similar PFMA prepolymers are in the range of $N_D^{25°\ C.} = 1.420$ to 1.460 which is compatible with many particulate glass fillers. Thus, composites based on PFMA and silanized fillers of the above type are translucent enough to be used as anterior restorations where esthetics are an important consideration. Composites prepared according to the dual silanization process according to the present invention, wherein filler is sequentially reacted with a silane coupling agent and fluorinated silane, are particularly preferred.

DETAILED DESCRIPTION OF THE INVENTION

The invention comprises dental resin systems including highly fluorinated alkyl methacrylate monomers or prepolymers, and dental materials, especially composites, prepared therefrom.

In one embodiment of the invention, the system includes a major portion of non-hydroxylated homolog or analog of bis-GMA, and a highly polyfluorinated alkyl monomethacrylate (PFMMA) as diluent monomer. Highly perfluorinated alkyl monomethacrylates of the formula I:

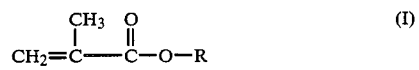

wherein R is $CH_2-(CF_2)_xF$ or $CH_2-(CF_2)_x-H$, and x is at least 5, usually from 2 to about 10, are preferred, especially the former, and most especially PDFOMA.

In another embodiment of the invention, the resin system is based on a highly polyfluorinated multifunctional methacrylate prepolymer (PFMA) preferably in combination with one or more diluent monomers to reduce viscosity; a number of diluent monomers unexpectedly function to increase strength of the system. The preferred multifunctional methacrylate prepolymer is PFMA according to the following formula II, in combination with one or more relatively hydrophobic fluorocarbon- or hydrocarbon-alkyl methacrylate monomer diluents of the type exemplified in Table I or II, below:

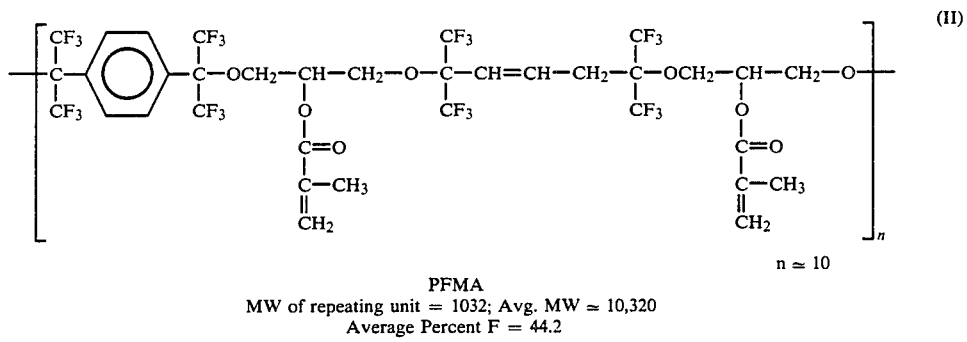

PFMA
MW of repeating unit = 1032; Avg. MW = 10,320
Average Percent F = 44.2

PFMA is a known compound described, e.g. in *J. Dent. Res.* 58: Spec. Issue A (1979).

Products according to the invention prepared from these dental systems include dental composites comprising polymeric matrices and silanized glass filler; preferably, silanized glass fluorosilanized according to the process of the invention is employed as filler for good composite strength.

The systems and composites of the present invention represent an improvement over prior art systems, retaining important water-related characteristics of the prior art materials, and also providing significantly improved physical and mechanical properties, especially good strength and dimensional stability.

PFMMA systems according to the invention are prepared by combining a minor proportion [less than about 15% (w/w), preferably from 5 to 12% (w/w)], of fluorinated monomethacrylate of the formula I (PFMMA) with a nonhydroxylated homolog or analog of bis-GMA; a preferred monomethacrylate of the formula I is 1,1-dihydropentadecafluorooctyl methacrylate (PDFOMA); preferred bis-GMA variants include 2,2-bis (p-beta-methacryloxy ethoxy) phenyl propane(bis-EMA) or an oligomeric urethane methacrylate containing a diluent monomer and known as a non-hydroxylated derivative of bis-GMA:

sive strengths (CS) (48 MPA and 253 MPA, respectively) but were not expecially hydrophobic.

PFMA systems according to the invention are prepared by blending a polyfluorinated multifunctional methacrylate (i.e. PFMA, one having a plurality of reactive vinyl groups) with a compatible diluent monomer to reduce prepolymer viscosity without adversely affecting valuable properties. Especially suitable monomers are relatively hydrophobic alkyl methacrylates, alkylene dimethacrylates or fluoroalkyl methacrylates of the types exemplified in Tables I and II. Alkyl groups containing from about 2–12 carbon atoms are especially contemplated with DMDMA, NPDMA and PDFOMA being particularly useful. Mixtures of diluent monomers are also used to advantage.

These systems have major amounts of hydrocarbon and/or fluorocarbon-diluent monomers (e.g. DMDMA, PDFOMA). Composites dereived from these PFMA resins have good mechanical properties (DTS=39 MPA and CS=188 MPA) and are extremely hydrophobic. The latter reflects the mechanically strong composites obtained from low surface energy polymeric binders.

Composites are suitably prepared by incorporating reinforcing filler into the polymerized or prepolymerized resin systems as known in the prior art. In the

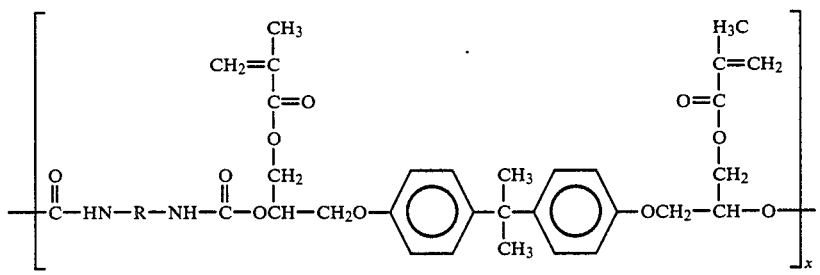

(Generalized chemical structure of the oligomeric urethane methacrylate component of the NCO monomer [bis-GMA(NCO)] which also contains a diluent monomer. R is an aliphatic hydrocarbon connecting group for the urethane functional groups.)

Attempts to prepare single phase formulations using high concentrations of PDFOMA and bis-EMA or the urethane derivative of bis-GMA were unsuccessful. With 1,10-decamethylene dimethacrylate (DMDMA) as a third monomer it was possible to obtain single phase formulations containing 8–11% by weight of PDFOMA. Composites prepared with PDFOMA resins had excellent diametral tensile (DTS) and comprespreferred embodiment of the invention, fluorosilanized glass is employed as filler. In order to preserve the strength of the composite, glass filler particles are silanized in known manner with a silane coupling agent, followed by silanization with a fluorinated silane agent such as 1,1,2,2,-tetrahydrotridecafluorooctyldimethyl chlorosilane; the resultant fluorosilanized glass is employed as filler in amounts of from about 25 to 85 wt. % of resin system, as exemplified in Table V. Suitable glass starting materials include commercial glass filler such as borosilicate glass powder, quartz, fused quartz and fused silica.

The following examples are included as illustrative of the invention.

EXAMPLES

Materials and Methods

The hydrocarbon and fluorocarbon monomers employed, with their names, abbreviations, chemical structures, molecular weights and sources are given in Tables I and II below. The amine polymerization accelerators employed are similarly listed in Table III below. In addition, some formulations contained the multifunctional chain transfer agent, pentaerythritol tetra(3-mercaptoproprionate), PETMP, and additional inhibitor in the form of BHA (2,6-di-tert-butyl-4-methylphenol). The synthesis of the polyfluoro-prepolymer multifunctional methacrylate, PFMA, was previously described (Antonucci, J. M.; New Monomers for Use in Dentistry, Organic Coatings and Plastic Chemistry (ACS) 42, 198-203, 1980; Antonucci, J. M.; New Monomers for Use in Dentistry, Biochemical and Dental Applications of Polymers, Eds. Gebelein, C. G. and Koblitz, F. F.; Plenum Press, N.Y., N.Y., 357-371, 1981). The chemical structure and some properties of PFMA are given above. A generalized representation of the chemical structure of the oligomeric urethane methacrylate in the NCO monomer, bis-GMA(NCO), is given above. This oligomeric monomer contains a diluent comonomer (e.g. triethylene glycol dimethacrylate).

EXAMPLE I

Resins Based on PDFOMA

Preliminary experiments to prepare a resin analogous to that derived from OFPMA (3)/bis-EMA (*J. Dent. Res.* 58: 1981-86, 1979) but using the more highly fluorinated PDFOMA in place of OFPMA were unsuccessful. The two monomers were incompatible at high concentrations (e.g. 20-70) of PDFOMA with phase separation occuring at ambient temperature. Similar results were obtained using bis-GMA (NCO) in place of bis-EMA and equally high concentrations of PDFOMA.

With DMDMA as a mutually miscible co-diluent it was possible to prepare bis-EMA/DMDMA resin formulations having 8-11 wt. % of PDFOMA. With bis-GMA (NCO) and DMDMA, similar amounts (8-10 wt. %) of PDFOMA were easily incorporated into resin formulations.

EXAMPLE II

Preparation of Reinforcing Filler (a) A-174 Silanized Glass with 1 wt. % Benzoyl Peroxide A commercial glass (Corning Glass, 7725, Corning Glass Works, Corning, N.Y.) powder containing barium oxide was silanized by a modification of a procedure described previously (*J. Dent. Res.* 61:1439-43, 1982 incorporated herein by reference). The glass powder was weighed into a round bottom flask and sufficient cyclohexane was added to give a loose slurry on swirling (e.g. 100 g of powder per 100 ml of cyclohexane). Based on the weight of the powder, a solution of 0.5 wt. % 3-methacryloxypropyltrimethoxysilane (A-174) (Corning Corp., N.Y., N.Y.) and 2.0 wt. % n-propylamine was added to the slurry and the flask was connected to a rotary evaporator. The slurry was mixed for one hour at atmospheric pressure at room temperature. After this period the flask was heated at 60°-65° C. by means of a water bath and moderate vacuum (20-30 mm Hg) was applied to the rotating flask. After the cyclohexane was removed, the flask was cooled to room temperature and the vacuum disconnected. The powdered silanized glass was swirled with fresh cyclohexane and the solvent decanted through a filter under a moderate vacuum. This procedure was repeated several times with fresh solvent in order to remove traces of the amine and soluble silane products. The glass powder was finally dried by exposure to a high vacuum (approximately 1 mm Hg) for 25 hours. The silanized glass was then coated with 1 wt. % benzoyl peroxide using a dilute solution of this peroxide in methylene chloride and the usual rotary evaporation procedure.

(b) Fluorosilanized glass (F-Glass) with 1 wt. % benzoyl peroxide

A portion of the previously silanized (A-174) glass was given a second silanization treatment with 0.5 wt. % of tridecafluoro-1,1,2,2-tetrahydrooctyldimethylchlorosilane (TDFOS) (Petrarch Systems, Inc., Bristol, PA) in cyclohexane containing 1 wt. % triethylamine by the same procedure used to prepare the A-174 silanized glass. The F-glass was then coated with 1 wt. % benzoyl peroxide by the deposition procedure previously described.

EXAMPLE III

Resins Based on PFMA (a) Formulation of Composites

Known powder/liquid formulation techniques were used to prepare glass filled composites according to the resin formulations shown in Tables IV and V. Filler was prepared according to Example II. Filler was blended with oligomer PFMA and diluent monomer and the admixture polymerized in known manner (Antonucci publications, supra, incorporated herein by reference).

(b) Evaluations of Composites (i) Setting Time.

The setting times of the various composite formulations were measured as described in ADA Specification No. 8 except that the specimen is transferred to the 100% relative humidity chamber at 37° C. one minute after mixing the powder and liquid components. Testing with the Gilmore needle commences after 1.5 min. from the start of the mix and continues every 0.5 min. until a setting time is determined.

(ii) Diametral Tensile Strength

The diametral tenside strengths of the composites were determined according to ADA Specification No. 27 (*JADA* 94:1191-94, 1977).

(iii) Compressive Strength

The compressive strengths of the composites were determined by a procedure similar to that employed for the determination of the diametral tensile strengths (*JADA* 94, op.cit.). Specimens were prepared in molds, 6 mm×12 mm, and crushed using a crosshead speed of 0.5 cm/min.

(iv) Water Sorption

The determination of water uptake of the composite specimens was performed in accordance with ADA Specification No. 27 (*JADA* 94, op.cit.). In addition, a new technique involving near infrared spectroscopy was used for measuring the water sorption of several thin composite specimens (50-100 μm) prepared by polymerization between crossed microscope slides (*Anal. Chem.* 33: 1947-47, 1961). Absorbance due to water occurs in a very transparent region of the near infrared spectrum at 5203-5220 cm$^{-1}$ (2.0-1.9 μm).

(c) Results

1. PDFOMA Based Composites

The setting times, diametral tensile strengths (DTS), compressive strengths (CS) and water sorption values of composites prepared from resin systems consisting of bis-EMA/DMDMA or bis-GMA (NCO)/DMDMA with relatively modest quantities (8–11 wt. %) of PDFOMA as a secondary diluent monomer are given in Table IV. The wt. % of covalently bound fluorine in this type of fluoro-resin system is only 4.9–6.8.

All composites had acceptable setting times and DTS values in excess of the minimum (34 MPa) required by the ADA Specification; CS values were in the range 178–253 MPa, typical of many conventional composites. Water sorption covered a range 0.28–0.72 mg/cm$^2$, also typical of many conventional composites. However, most of the values tended toward the low end of the water sorption scale.

One unexpected consequence of using PDFOMA in these formulations was a significant increase in the setting times of the usually very reactive resins based on bis-EMA or bis-GMA(NCO) and DMDMA. For example, a resin system consisting of equal parts by weight of bis-GMA(NCO) and DMDMA with 0.4 wt. % BDMA and 0.1 BHT wt. % set in less than a minute when mixed with 3 parts of silanized glass coated with 1 wt. % benzoyl peroxide. Similar formulations with 8–10 wt. % PDFOMA had markedly longer setting times (5–7, Table IV). By contrast, the replacement of PDFOMA by n-octyl methacrylate (OMA), the hydrocarbon analog of PDFOMA in the bis-GMA(NCO)/DMDMA monomer system resultd in composites with shorter setting times (9 and 10, Table IV). 9 contains an amount of OMA (4.05 wt. %) equivalant in molality to the PDFOMA in 7, Table IV. 10 (Table IV) which had the lowest water sorption (0.28 mg/cm$^2$) of all the bis-GMA(NCO)/DMDMA composites contains more than twice this molal concentration of OMA. It was not possible to prepare a single phase formulation of this resin system with an equivalent amount (approx. 20 wt. %) of PDFOMA.

It is believed that resin formulations containing significant quantities of highly fluorinated monomers such as PDFOMA may dissolve more oxygen than hydrocarbon resin systems and, therefore, may be more sensitive to air inhibition. This inhibitory effect can be compensated by the use of higher concentrations of the amine polymerization accelerator (e.g. 5, Table IV). The esthetics and color stability of the composite were compromised by this approach. A more satisfactory solution is to use modest amounts of the high molecular weight, multifunctional chain transfer agent, PETMP, which functions both as a synergistic accelerator, reactive diluent and agent for ameliorating the effects of air inhibition. The esthetics, color stabilities and mechanical properties of composites prepared with PETMP were superior to those prepared without the polythiol.

The use of the dual silanized F-glass as a filler was not effective in reducing water uptake but, in some cases, an improvement in mechanical strength was noted (compare 3, 4, 5, 6, 8A Table IV). With fluoro-resin systems, especially those of high fluorine content (e.g. PFMA), it was found that F-glass facilitated the mixing of powder/liquid formulations.

2. PFMA Based Composites

The setting times, DTS and some CS and water sorption values for composites prepared from resin systems utilizing PFMA as the major monomeric component are given in Table 5. The wt. % of covalently bound fluorine ranged fron 30.4 to 41.5 for this type of fluoro-resin system.

As can be seen from Table V, a great variety of diluent monomers can be used with PFMA ranging from MMA to bis-EMA. In addition fluorocarbon methacrylates such as OFPMA and PDFOMA also are compatible with PFMA. All the composites had suitable working characteristics and setting times. The 24 hour DTS values are in the 30–40 MPa range, but with most formulations giving composites exceeding the ADA minimum of 34 MPa. Formulation 6A which a somewhat deficient 24 hour DTS of 32.3 MPa increased in strength to about 36 MPa after 48 hours (Table V). Similar increases in strength with time were noted for formulation 31 (24 h DTS=39; 1 W DTS=42 MPa) and for formulation 4 (24 h DTS=38, 2W DTS=39 MPa). Formulation 31 also had remarkably low water sorption (Table V). Formulations 3H, 7A and 7B (Table V) had CS values of 165, 159 and 188, respectively, which are similar to those of some conventional composites. The water sorption values are in the exceedingly low range of 0.13–0.23 mg/cm$^2$, similar to that of the hydrophobic composites based on OFPMA/bis-EMA. Preferred difunctional methacrylate hydrocarbon diluent monomers are NPDMA, DMDMA, HMDMA, bis-MA and bis-EMA. Some of these monomers require the use of a second diluent monomer to be effective. The trifunctional methacrylate, TMPTMA, which gave high strength composites with bis-GMA, failed to strengthen similar PFMA composites.

The use of binary or ternary diluent systems for PFMA often resulted in an increase in strength properties of the fluoro-composite. For example, formulation 1 which employed only MMA as a diluent yields a composite with a DTS of 31 MPa whereas formulation 2, which also utilized NPDMA and PETMP gave significantly higher strength (DTS=40 MPa) materials (Table V). The use of a second crosslinking diluent such as NPDMA and TMPTMA should have a similar strengthening effect on PFMA/TMPTMA based composites.

The use of PETMP aided the esthetics, color stability and, often, the strength properties of these composites. With modest amounts of PETMP less of the amine polymerization accelerator is required to obtain the same setting time and at least equivalent DTS values (compare 3A and 3B with 3C and 3D, Table V). With PETMP and the same content of amine accelerator, shorter setting times and higher DTS values are obtained (Compare 3F and 3G with 3H and 3I, Table V).

As part of a binary or ternary diluent monomer systems, the bulky solid dimethacrylates, bis-MA and bis-EMA, were miscible with PFMA (4, 10A, 10B, 10C, Table V). In formulation 10A, the very fluid hydrophobic resin, OFPMA (3)/bis-EMA (1) of Craig et al (e.g. U.S. Pat. No. 4,292,029; J. Dent Res. 58: 1981–86, 1979) was used as the diluent for PFMA and gave composites of good strength (DTS=38 MPa). A variant of this formulation (10B, 10C) using a ternary diluent system of OFPMA, bis-EMA and NPDMA also gave hydrophobic composites of good strength (DTS=38 and 40 MPa, respectively.) 9A and 9B (Table V) which used HFIPMA as the major diluent monomer and NPDMA as the minor diluent monomer for PFMA also gave hydrophobic composites with good strength properties. 7A and 7B, (Table 5) which used DMDMA as the only diluent monomer, gave composites with good strength properties and extremely low water uptake. As noted above, the use of F-glass did not enhance the hydrophobicity of the composite system but did improve the ease of mixing of these powder/liquid formulations.

(d) Water Sorption by Near-Infrared Spectroscopy

In contrast to determination of water sorption by the method outlined in ADA Specification No. 27 which requires immersion of relatively large specimens in water, correction for solubility effects, long equilibration times and the measurement of small changes in large numbers, the near-IR method has the following advantages: (1) thin films which have short equilibration times are used, (2) comparative measurements after immersion in water versus simple exposure to atmospheres of 100% relative humidity (which eliminates leaching or solubility effects) can be made and (3) the time dependent water-sorption behavior of the specimen may be easily monitored. The spectra obtained indicate the sensitivity of this method.

The extreme reluctance to water uptake by the composite film derived from PFMA (3H, Table V) is made strikingly evident by the absence of any absorbance peak for water after the dry composite film is exposed to the same humid atmosphere for 24 hours.

As expected, water-related properties, such as water sorption, for these PFMA based composites are similar to the hydrophobic composites reported by Craig et al. The significantly greater mechanical strength of the PFMA derived composites compared to those derived from OFPMA/bis-EMA probably is a conseqience of the greater degree of crosslinking possible with the PFMA based resins which yields polymeric matrices of higher glass transition temperatures than those obtainable with the OFPMA/bis-EMA monomer system.

Due to the prepolymer nature of principal monomeric component, PFMA, and its relatively low viscosity, PFMA based composites and sealants exhibit rather low polymerization contraction.

TABLE I

Hydrocarbon Monomers

| Name | Abbreviation | Chemical Structure | Molecular Weight | Source |
|---|---|---|---|---|
| Methyl Methacrylate | MMA | $CH_2=C(CH_3)-C(=O)-OCH_3$ | 100 | Aldrich Chemical Co. Milwaukee, WI |
| Neopentyl Dimethacrylate | NPDMA | $CH_2=C(CH_3)-C(=O)-O-CH_2-C(CH_3)_2-CH_2-O-C(=O)-C(CH_3)=CH_2$ | 240 | Esschem Essington, PA |
| 1,10-Decamethylene Dimethacrylate | DMDMA | $CH_2=C(CH_3)-C(=O)-O-(CH_2)_{10}-O-C(=O)-C(CH_3)=CH_2$ | 310 | Esschem Essington, PA |
| 1,6-Hexamethylene Dimethacrylate | HMDMA | $CH_2=C(CH_3)-C(=O)-O(CH_2)_6OC(=O)-C(CH_3)=CH_2$ | 254 | Esschem Essington, PA |
| n-Octyl Metahcrylate | OMA | $CH_2=C(CH_3)-C(=O)-(CH_2)_7-CH_3$ | 198 | Polysciences, Inc. Warrington, PA |
| 2,2-BIS[p-(Methacryloxy) Phenyl] Propane | BIS-MA | $[CH_2=C(CH_3)-C(=O)-O-C_6H_4-]_2C(CH_3)_2$ | 364 | Polysciences, Inc. Warrington, PA |
| 2,2-Bis[p-(Methacryloxyethyloxy) Phenyl] Propane | BIS-EMA | $[CH_2=C(CH_3)-C(=O)-OCH_2CH_2O-C_6H_4-]_2C(CH_3)_2$ | 444 | ESPE GAMBL Seefeld, Germany |
| Trimethylol Propane Trimethacrylate | TMPTMA | $CH_3CH_2-C[-CH_2O-C(=O)-C(CH_3)=CH_2]_3$ | 338 | ESSCHEM Essington, PA |
| NCO Monomer | BIS-GMA (NCO) | See Text | >1000 | L. D. Caulk Co. Milford, DE |

TABLE II

Fluorocarbon Monomers

| Name | Abbreviation | Chemical Structure | Molecular Weight | Source |
|---|---|---|---|---|
| Hexafluoroisopropyl Methacrylate | HFIPMA | $CH_2=C(CH_3)-C(=O)-O-CH(CF_3)_2$ | 236 | Columbia Organic Chemicals, Columbia, SC |
| Octafluoropentyl Methacrylate | OFPMA | $CH_2=C(CH_3)-C(=O)-O-CH_2-(CF_2)_4-H$ | 300 | PCR Research Chemicals, Inc., Gainesville, FL |
| Pentadecafluorooctyl Methacrylate | PDFOMA | $CH_2=C(CH_3)-C(=O)-OCH_2-(CF_2)_7-F$ | 468 | Columbia Organic Chemicals, Columbia, SC |
| Polyfluorinated Polymethacrylate | PFMA | See formula II | 10,320 | Synthesized |

TABLE III

Polymerization Accelerators

| Name | Abbreviation | Chemical Structure | Molecular Weight | Source |
|---|---|---|---|---|
| p-Tert-Butyl-N,N—Dimethylaniline | BDMA | $(CH_3)_3C-C_6H_4-N(CH_3)_2$ | 177 | Aldrich Chemical Co. Milwaukee, WI |
| P—N,N—Dimethylaminophenethanol | DMAPE | $(CH_3)_2N-C_6H_4-CH_2CH_2OH$ | 165 | Aldrich CHemical Co. Milwaukee, WI |
| N,N—Dimethyl-sym-xylidine | DMSX | $(CH_3)_2N-C_6H_3(CH_3)_2$ | 149 | Aldrich Chemical Co. Milwaukee WI |
| P—N,N—Diethyl-aminophenylacetic Acid | DEAPAA | $(CH_3CH_2)_2N-C_6H_4-CH_2CO_2H$ | 207 | Synthesized |

TABLE IV

COMPOSITION AND PROPERTIES OF EXPERIMENTAL COMPOSITES FORMULATED WITH BIS-EMA OR BIS-GMA/NCO AND DMDMA AND PDFDMA

| Form No. | Liquid Composition WT % | | Setting Time (Min) | Strength, MPa | | Water Sorption (mg/cm$^2$) | % F in Resin |
|---|---|---|---|---|---|---|---|
| | | | | Diametral Tensile[a] | Compressive[a] | | |
| 1 | BIS-EMA | 44.31 | 5.0 | 36.0 (2.8)[b] | 174 (4) | — | 6.8 |
|   | DMDMA | 44.31 | | | | | |
|   | PDFOMA | 11.15 | | | | | |
|   | BDMA | 0.23 | | | | | |
| 2 | BIS-EMA | 44.25 | 3.5 | 41.0 (3.0) | 208 (27) | 0.72 (0.16) | 6.8 |
|   | DMDMA | 44.25 | | | | | |
|   | PDFOMA | 11.15 | | | | | |
|   | BDMA | 0.35 | | | | | |
| 3 | BIS-EMA | 49.25 | 3.0 | 43.2 (1.2) | — | 0.28 (0.02) | 5.6 |
|   | DMDMA | 41.25 | | 48.5 (3.5)[c] | | 0.32 (0.01)[c] | |
|   | PDFOMA | 9.30 | | | | | |
|   | BDMA | 0.20 | | | | | |
| 4 | BIS-EMA | 45.91 | 3.0 | 43.4 (2.9) | — | — | 4.9 |
|   | DMDMA | 45.91 | | 41.0 (3.1)[c] | | | |
|   | PDFOMA | 7.98 | | | | | |
|   | BDMA | 0.20 | | | | | |

TABLE IV-continued
COMPOSITION AND PROPERTIES OF EXPERIMENTAL COMPOSITES FORMULATED WITH BIS-EMA OR BIS-GMA/NCO AND DMDMA AND PDFDMA

| Form No. | Liquid Composition WT % | | Setting Time (Min) | Strength, MPa Diametral Tensile[a] | Compressive[a] | Water Sorption (mg/cm$^2$) | % F in Resin |
|---|---|---|---|---|---|---|---|
| 5 | BIS-GMA/NCO | 51.58 | 4.5 | 40.5 (2.9)[b] | 232 (8)[b] | 0.41 (0.14) | 4.9 |
|  | DMDMA | 39.84 |  | 46.3 (2.2)[c] | 248 (10)[c] | 0.36 (0.14)[c] |  |
|  | PDFOMA | 8.07 |  |  |  |  |  |
|  | BDMA | 0.41 |  |  |  |  |  |
|  | BHT | 0.10 |  |  |  |  |  |
| 6 | BIS-GMA/NCO | 54.77 | 4.0 | 42.8 (4.6) | — | — | 4.6 |
|  | DMDMA | 33.48 |  | 45.7 (2.3)[c] |  |  |  |
|  | PDFOMA | 9.18 |  |  |  |  |  |
|  | PETMP | 2.22 |  |  |  |  |  |
|  | BDMA | 0.25 |  |  |  |  |  |
|  | BHT | 0.10 |  |  |  |  |  |
| 7 | BIS-GMA/NCO | 58.55 | 4.5 | 40.3 (3.3) | 210 (16) | 0.71 (0.05) | 5.5 |
|  | DMDMA | 31.68 |  |  |  |  |  |
|  | PDFOMA | 9.02 |  |  |  |  |  |
|  | BDMA | 0.57 |  |  |  |  |  |
|  | BHT | 0.18 |  |  |  |  |  |
| 8 | BIS-GMA/NCO | 57.70 | 4.5 | 46.1 (3.3) | 253 (4) | 0.43 (0.03) | 5.4 |
|  | DMDMA | 31.06 |  | 45.5 (5.2)[c] | 251 (16)[c] | 0.57 (0.03)[c] |  |
|  | PDFOMA | 8.87 |  |  |  |  |  |
|  | PETMP | 1.99 |  |  |  |  |  |
|  | BDMA | 0.20 |  |  |  |  |  |
|  | BHT | 0.18 |  |  |  |  |  |
| 9 | BIS-GMA/NCO | 62.20 | 2.5 | 41.7 (4.1) | 221 (4) | 0.36 (0.05) | 0 |
|  | DMDMA | 33.45 |  |  |  |  |  |
|  | OMA* | 4.05 |  |  |  |  |  |
|  | BDMA | 0.20 |  |  |  |  |  |
|  | BHT | 0.10 |  |  |  |  |  |
| 10 | BIS-GMA/NCO | 50.90 | 2.0 | 34.8 (4.5) | 165 | 0.28 (0.09) | 0 |
|  | DMDMA | 39.47 |  |  |  |  |  |
|  | OMA | 8.97 |  |  |  |  |  |
|  | EDMA | 0.36 |  |  |  |  |  |
|  | BHT | 0.30 |  |  |  |  |  |

*OMA = n-Octyl Methacrylate, Hydrocarbon Analog of PDFOMA
[a]Average of 5 determinations
[b]Standard Deviation
[c]Using F-Glass

TABLE V
Composition and Properties of Experimental Composites Based on PFMA

| Form No. | Liquid Composition (wt. %) | | P/L Ratio[c] | Setting Time (min) | Strength (MPa) Diametral Tensile (std. dev.)[a] | Compressive (std. dev.)[a] | Water Sorption (mg/cm$^2$) | Wt. Percent F in Resin |
|---|---|---|---|---|---|---|---|---|
| 1 | PFMA | 86.55 | 3 | 5.0 | 30.9 (1.1)[b] | — | — | 38.3 |
|  | MMA | 12.91 |  |  |  |  |  |  |
|  | DMAPE | 0.54 |  |  |  |  |  |  |
| 2 | PFMA | 72.80 | 3.5 | 2.5 | 39.7 (2.8) | — | — | 32.2 |
|  | NPDMA | 14.00 |  |  |  |  |  |  |
|  | MMA | 10.80 |  |  |  |  |  |  |
|  | PETMP | 2.00 |  |  |  |  |  |  |
|  | DMAPE | 0.40 |  |  |  |  |  |  |
| 3A | PFMA | 70.50 | 3.5 | 3.0 | 34.0 (3.3) | — | — | 31.2 |
|  | NPDMA | 29.10 |  |  |  |  |  |  |
|  | DMAPE | 0.40 |  |  |  |  |  |  |
| 3B | PFMA | 70.45 | 3.5 | 3.0 | 36.5 (1.2) | — | — | 31.1 |
|  | NPDMA | 29.09 |  |  |  |  |  |  |
|  | DMAPE | .45 |  |  |  |  |  |  |
| 3C | PFMA | 69.59 | 3.5 | 3.5 | 35.6 (3.0) | — | — | 30.8 |
|  | NPDMA | 28.70 |  |  |  |  |  |  |
|  | PETMP | 1.55 |  |  |  |  |  |  |
|  | DMAPE | 0.16 |  |  |  |  |  |  |
| 3D | PFMA | 69.51 | 3.5 | 3.0 | 38.7 (0.9) | — | — | 30.7 |
|  | NPDMA | 28.62 |  |  |  |  |  |  |
|  | PETMP | 1.55 |  |  |  |  |  |  |
|  | DMAPE | 0.28 |  |  |  |  |  |  |
| 3E | Same as 3D with F-Glass |  | 3.5 | 3.0 | 38.8 (1.2) | — | — | 30.7 |
| 3F | PFMA | 70.00 | 3.5 | 5.0 | 35.5 (0.2) | — | — | 30.9 |
|  | NPDMA | 29.55 |  |  |  |  |  |  |
|  | DEAPAA | 0.45 |  |  |  |  |  |  |
| 3G | PFMA | 69.90 | 3.5 | 4.5 | 35.7 (2.5) | — | — | 30.9 |
|  | NPDMA | 29.50 |  |  |  |  |  |  |
|  | DEAPAA | 0.60 |  |  |  |  |  |  |
| 3H | PFMA | 68.87 | 3.5 | 3.0 | 38.7 (2.5) | 188 (20) | 0.20 (0.03) | 30.4 |

TABLE V-continued

Composition and Properties of Experimental Composites Based on PFMA

| Form No. | Liquid Composition (wt. %) | | P/L Ratio[c] | Setting Time (min) | Strength (MPa) Diametral Tensile (std. dev.)[a] | Compressive (std. dev.)[a] | Water Sorption (mg/cm$^2$) | Wt. Percent F in Resin |
|---|---|---|---|---|---|---|---|---|
| | NPDMA | 29.06 | | | | | | |
| | PETMP | 1.62 | | | | | | |
| | DEAPAA | 0.45 | | | | | | |
| 3I | PFMA | 69.20 | 3.5 | 3.0 | 39.2 (2.3) | — | 0.15 (0.02) | 30.6 |
| | NPDMA | 29.20 | | | 42.4 (1.0)* | | | |
| | PETMP | 1.00 | | | | | | |
| | DEAPAA | 0.60 | | | | | | |
| 4 | PFMA | 70.60 | 3.5 | 4.0 | 37.6 (1.0) | — | 0.19 (0.01) | 31.0 |
| | NPDMA | 19.07 | | | 39.1 (2.3)** | | | |
| | BIS-MA | 9.62 | | | | | | |
| | PETMP | 0.97 | | | | | | |
| | DMAPE | .28 | | | | | | |
| 5 | PFMA | 59.00 | 3 | 4.0 | 36.4 (3.0) | — | — | 35.3 |
| | PDFOMA | 15.20 | | | | | | |
| | HMDMA | 15.20 | | | | | | |
| | BIS-EMA | 10.00 | | | | | | |
| | DMSX | 0.60 | | | | | | |

*Stored 1 week in distilled water at 37° C.
Stored 2 weeks in distilled water at 37° C.

| Form No. | Liquid Composition (wt. %) | | P/L Ratio[c] | Setting Time (min) | Strength (MPa) Diametral Tensile (std. dev.)[a] | Compressive (std. dev.)[a] | Water Sorption (mg/cm$^2$) | Wt. Percent F in Resin |
|---|---|---|---|---|---|---|---|---|
| 6A | PFMA | 78.15 | 3 | 2.0 | 32.3 (3.0)[b] | — | 0.15 (0.02) | 34.5 |
| | DMDMA | 18.49 | | | 35.6 (2.4)*** | | | |
| | PETMP | 3.13 | | | | | | |
| | BDMA | 0.23 | | | | | | |
| 6B | Same as 6A with F-Glass | | 3 | 2.0 | 32.0 (1.6) | — | 0.23 (0.01) | 34.5 |
| 7A | PFMA | 74.33 | 3.5 | 4.0 | 35.8 (2.9) | 165 (29) | 0.13 (0.01) | 32.9 |
| | DMDMA | 24.86 | | | | | | |
| | PETMP | 0.54 | | | | | | |
| | BDMA | 0.27 | | | | | | |
| 7B | Same as 7A with F-Glass | | 3.5 | 4.0 | 35.3 (2.0) | 159 (14) | 0.16 (0.03) | 32.9 |
| *7C | PFMA | (68.84) | 3 | 2.0 | 41.0 (1.0)[b] | 232 (9)[b] | 0.17 (0.02) | 30.4 |
| | DMDMA | (29.50) | | | | | | |
| | PETMP | (0.98) | | | | | | |
| | **DHPPT | (0.40) | | | | | | |
| | DMAPE | (0.28) | | | | | | |
| *7D | PFMA | (69.53) | 3 | 6.0 | 39.0 (1.0) | — | 0.18 (0.02) | 30.4 |
| | DMDMA | (29.79) | | | | | | |
| | DHPPT | (0.40) | | | | | | |
| | DMAPE | (0.28) | | | | | | |
| 7E | Same | | 3 | 6.0 | 36.0 (6) | — | 0.21 (0.02) | 30.4 |
| 7F | Same | | 4 | 5.0 | 41.0 (3) | — | 0.18 (0.02) | 30.4 |
| 8A | PFMA | 71.50 | 3.5 | 4.5 | 30.7 (2.5) | — | — | 31.6 |
| | TMPTHA | 27.20 | | | | | | |
| | PETMP | 1.00 | | | | | | |
| | DMAPE | 0.30 | | | | | | |
| 8B | PFMA | 75.50 | 3.5 | 3.5 | 29.8 (1.1) | | | 34.9 |
| | TMPTMA | 20.60 | | | | | | |
| | PDFOMA | 2.50 | | | | | | |
| | PETMP | 1.00 | | | | | | |
| | DMAPE | 0.30 | | | | | | |
| | BHT | 0.10 | | | | | | |
| 9A | PFMA | 69.10 | 3.5 | 4.5 | 35.3 (3.0) | | | 41.0 |
| | HFIPMA | 21.80 | | | | | | |
| | NPDMA | 8.40 | | | | | | |
| | DMAPE | 0.70 | | | | | | |
| 9B | PFMA | 68.30 | 3.5 | 3.0 | 39.6 (1.2) | | 0.20 (0.03) | 40.6 |
| | HFIPMA | 21.60 | | | | | | |
| | NPDMA | 8.30 | | | | | | |
| | PETMP | 1.10 | | | | | | |
| | DMAPE | 0.70 | | | | | | |
| 10A | PFMA | 68.10 | 4.0 | 7.5 | 37.7 (1.7) | — | — | 41.5 |
| | OFPMA | 22.40 | | | | | | |
| | BIS-EMA | 7.50 | | | | | | |
| | PETMP | 1.40 | | | | | | |
| | DMAPE | 0.60 | | | | | | |
| 10B | PFMA | 66.72 | 3.5 | 5.0 | 38.4 (1.8) | — | — | 38.3 |
| | OFPMA | 17.44 | | | | | | |
| | BIS-EMA | 5.83 | | | | | | |
| | NPDMA | 8.67 | | | | | | |
| | PETMP | 0.90 | | | | | | |
| | DMAPE | 0.44 | | | | | | |
| 10C | Same as 10B | | 4.0 | 2.5 | 40.0 (2.8) | 0.21 (0.01) | | 38.3 |
| 11 | PFMA | (69.27) | 4.5 | 6.5 | 40.0 (1) | — | 0.17 (0.02) | 30.4 |
| | HMDMA | (28.08) | | | | | | |
| | PETMP | (1.32) | | | | | | |
| | DHPPT | (0.58) | | | | | | |

TABLE V-continued

| | Composition and Properties of Experimental Composites Based on PFMA | | | | | | |
|---|---|---|---|---|---|---|---|
| Form No. | Liquid Composition (wt. %) | P/L Ratio$^c$ | Setting Time (min) | Strength (MPa) | | Water Sorption (mg/cm$^2$) | Wt. Percent F in Resin |
| | | | | Diametral Tensile (std. dev.)$^a$ | Compressive (std. dev.)$^a$ | | |
| | DMAPE (0.58) BHT (0.17) | | | | | | |

*Fused quartz silanized with A-174 and coated with 1% BP used in these formulations
**DHPPT = N,N—Bis(2-Hydroxypropyl)p-toluidine
***Stored in distilled water for 48 hours at 37° C.
$^a$mean of 5 determinations; 24 hour storage at 37° C.
$^b$standard deviation
$^c$except for composites employing F = Glass, powder was glass silanized with 3-methacryloxypropyltrimethoxysilane (A-174) and coated with 1 wt % benzoyl peroxide (see Table 4)

It will be obvious to those skilled in the art that various changes may be made without departing from the scope of the invention and the invention is not to be considered limited to what is shown in the drawings and described in the specification.

What is claimed is:

1. A dental composition comprising a resinifiable mixture, wherein said mixture comprises a major portion of a polyfluorinated polyfunctional methacrylate prepolymer according to the following formula:

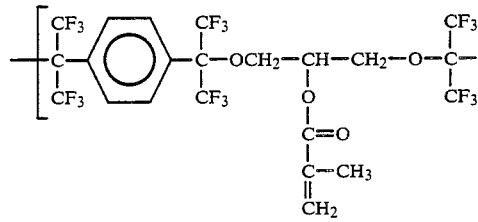

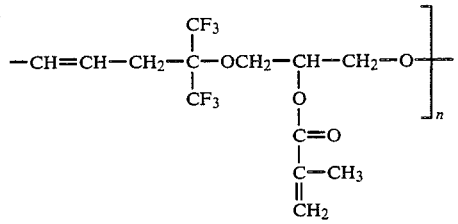

wherein n is an integer averaging about 10, and a minor portion of a diluent monomer selected from the group consisting of compatible alkyl methacrylates, unsubstituted alkylene dimethacrylates and fluoroalkyl methacrylates.

2. The composition of claim 1 wherein said diluent monomer is a compatible alkyl or fluoroalkyl methacrylate.

3. The composition of claim 1 wherein the diluent monomer is an unsubstituted alkylene dimethacrylate.

4. The composition of claim 3 wherein the diluent monomer is neopentyl dimethacrylate; 1,10-decamethylene dimethacrylate; 1,6-hexamethylene dimethacrylate; 2,2-bis[p-(methacryloxy)phenyl]propane; 2,2-bis[p-(methacryloxyethoxy)phenyl]propane; or a mixture thereof.

5. The resin composition of claim 1, wherein said polyfunctional methacrylate prepolymer is present in an amount of more than about 70% by weight of the composition.

* * * * *

UNITED STATES PATENT AND TRADEMARK OFFICE
CERTIFICATE OF CORRECTION

PATENT NO. : 4,616,073
DATED : October 7, 1986
INVENTOR(S) : Joseph M. Antonucci It is certified that error appears in the above-identified patent and that said Letters Patent is hereby corrected as shown below:

[57] ABSTRACT: correct the fifth line of the Abstract to read:
--functional methacrylate (PFPMA) such as PFMA, preferably in--

Correct the spelling of the word spanning lines 54 and 55 in column 1 to read: --intraorally--

Signed and Sealed this

Third Day of March, 1987

*Attest:*

DONALD J. QUIGG

*Attesting Officer*    *Commissioner of Patents and Trademarks*